(12) United States Patent  
Earhart et al.

(10) Patent No.: US 7,704,426 B2
(45) Date of Patent: Apr. 27, 2010

(54) PROCESS FOR CREATING A STOP SURFACE ON A SYRINGE PLUNGER ROD

(75) Inventors: Stephen Earhart, Crestwood, MO (US); Richard L. Fiser, Wildwood, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 20 days.

(21) Appl. No.: 12/004,320

(22) Filed: Dec. 20, 2007

(65) Prior Publication Data
US 2008/0167625 A1 Jul. 10, 2008

Related U.S. Application Data

(60) Provisional application No. 60/877,757, filed on Dec. 29, 2006.

(51) Int. Cl.
*B29C 59/02* (2006.01)
(52) U.S. Cl. .................. 264/230; 264/293; 604/218; 604/181
(58) Field of Classification Search ................. 264/154, 264/155, 293, 230; 604/218, 181
See application file for complete search history.

(56) References Cited

U.S. PATENT DOCUMENTS

| | | | |
|---|---|---|---|
| 2,217,609 A | | 10/1940 | Bierman |
| 4,950,442 A | * | 8/1990 | Tanimoto et al. ............. 264/489 |
| 5,876,382 A | * | 3/1999 | Erickson ..................... 604/198 |
| 6,050,977 A | | 4/2000 | Adams |
| 6,494,866 B1 | | 12/2002 | Robinson |
| 2004/0261912 A1 | | 12/2004 | Wu |

FOREIGN PATENT DOCUMENTS

GB 0 542 619 1/1942

OTHER PUBLICATIONS

PCT International Search Report for International Application No. PCT/US07/26051 dated May 15, 2008 (3 pgs.).

* cited by examiner

*Primary Examiner*—Joseph S Del Sole
*Assistant Examiner*—John P Robitaille (57) ABSTRACT

A process for creating a stop surface on a plunger rod of a syringe is disclosed. The process includes the step of providing a preformed or molded plunger rod, and the step of forming a radially-extending deformation on the molded plunger rod. The presently disclosed in-line process allows for the use of a single molding rod to form plunger rods having one or more selectively located stop positions.

9 Claims, 7 Drawing Sheets

PROCESS FOR CREATING A STOP SURFACE ON A SYRINGE PLUNGER ROD

CROSS REFERENCE TO RELATED APPLICATIONS

This application claims priority from U.S. provisional application Ser. No. 60/877,757, filed Dec. 29, 2006, the entirety of which is incorporated herein by reference.

BACKGROUND

1. Technical Field

The present disclosure relates to a process for creating a stop surface on a syringe. More specifically, the present disclosure relates to an in-line process for creating a stop surface on the plunger rod of a syringe.

2. Background of Related Art

Figure 1:
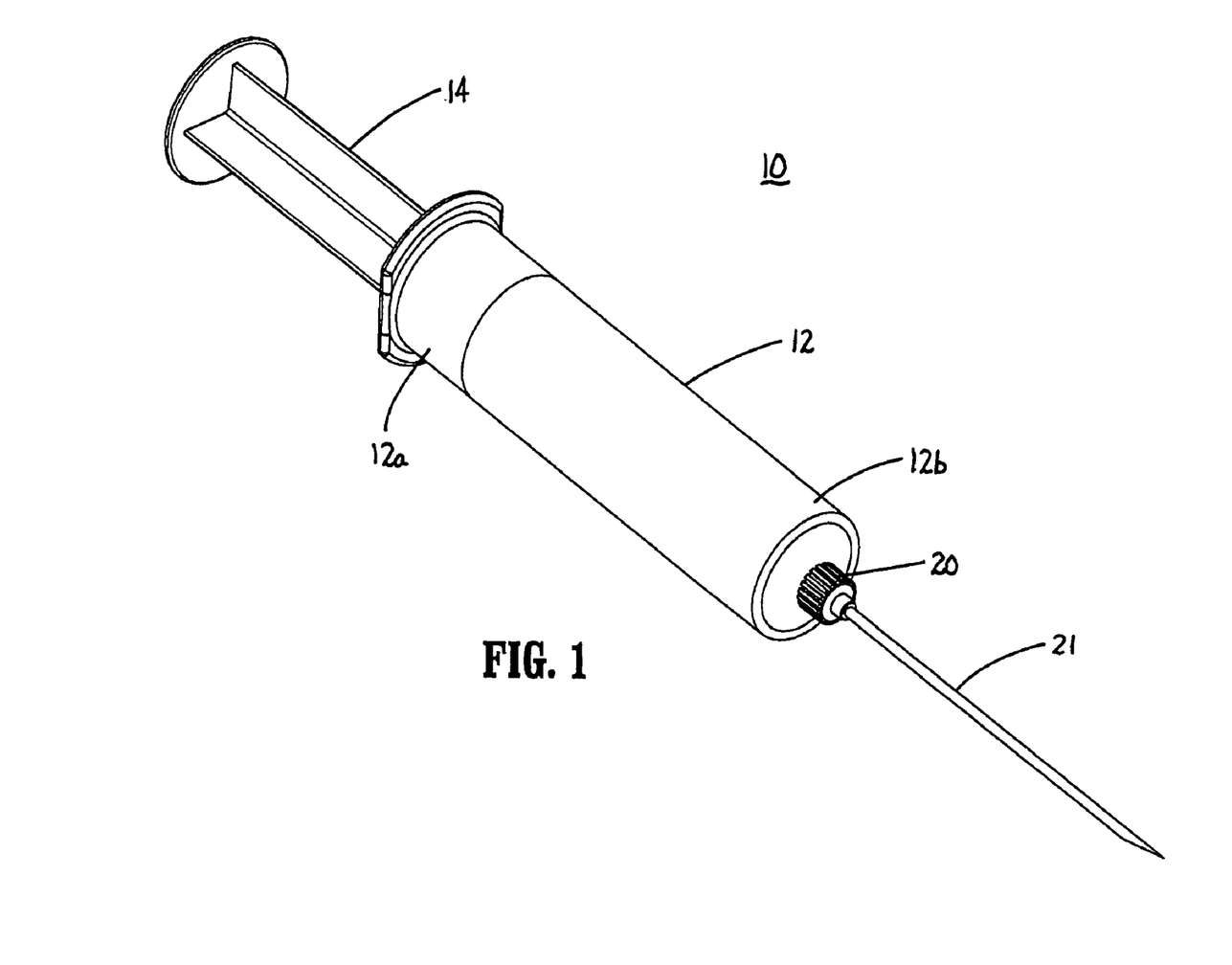
FIG. 1 is a side perspective view from the distal end of a "Prior Art" syringe.
Figure 2:
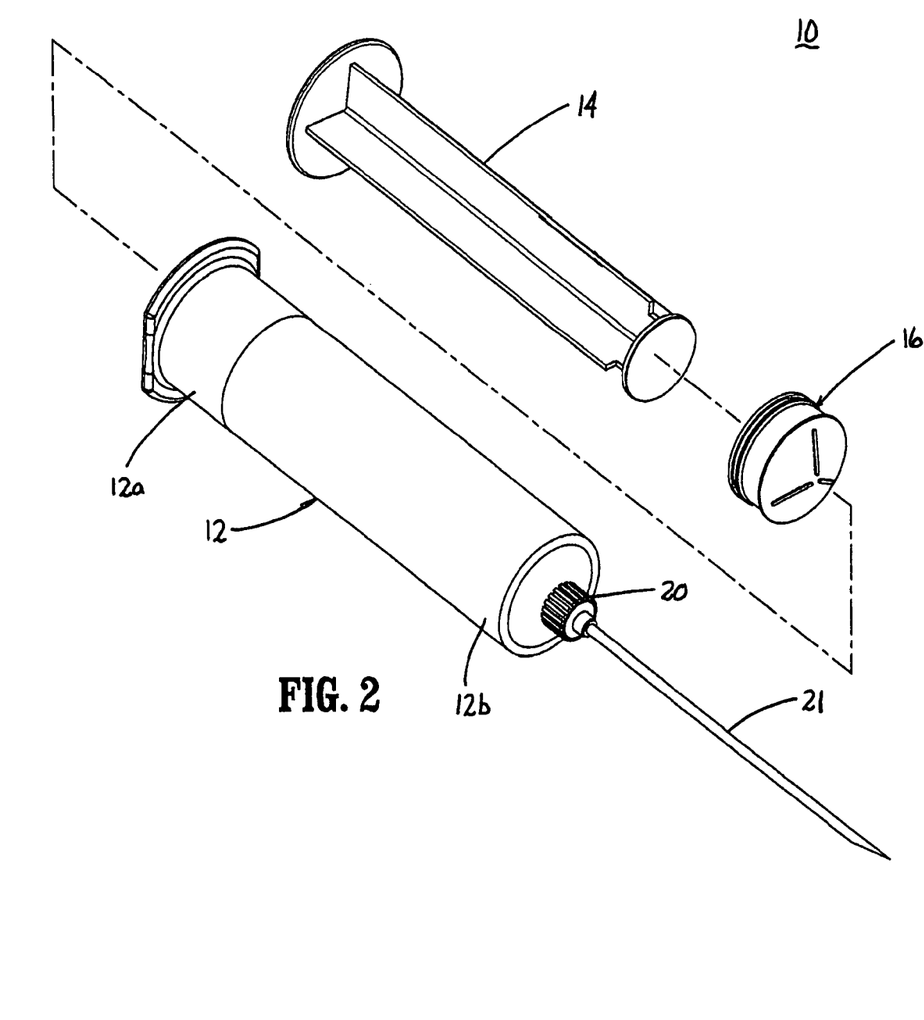
FIG. 2 is a side perspective exploded view from the distal end of the syringe shown in FIG. 1.

Referring to FIGS. 1 and 2, standard syringes 10 typically include a syringe barrel 12, a plunger rod 14 and a plunger tip 16 (FIG. 2). A proximal end 12a of syringe barrel 12 defines a circular opening dimensioned to slidably receive plunger tip 16 and plunger rod 14. Typically, the distal end 12b of barrel 12 defines a small diameter opening and a connector 20, e.g., a luer type connector, for securing syringe barrel 12 to a medical device, e.g., a needle 21, a catheter, a blood collection device, etc.

It is known in the syringe arts to provide limiting structure within a syringe barrel 12 and/or on a plunger rod 14 to limit or restrict the extent of movement of the plunger in relation to the barrel of the syringe. Generally, the limiting structure is integrally formed on the syringe barrel and/or plunger rod during the molding operation of the syringe barrel and/or plunger rod. As such, changing the location of the position of the limiting structure requires a different molding tool for each stop position. This can be costly and time consuming.

The present disclosure is directed to a new process for creating limiting structure, i.e., a stop member, on a syringe plunger rod. As will be described in detail below, the presently disclosed process allows the design of the plunger rod to be modified in an inline process, after the initial molding process has been completed, such that limiting structure can be provided on the plunger rod to selectively define one or more stop positions at selective locations along the plunger rod. By providing such an inline process, a single molding tool can be used to form plunger rods with one or more selectively located stop positions. Further, a single plunger rod design can be molded and inventoried and later subjected to the in-line process to make plunger rods having stop positions at a variety of different positions.

BRIEF DESCRIPTION OF EMBODIMENTS

Embodiments of the presently disclosed process for creating a stop on a syringe plunger rod are disclosed herein with reference to the drawings, wherein.

DETAILED DESCRIPTION

Embodiments of the presently disclosed Process For Creating A Stop On a Syringe Plunger Rod will now be described in detail with reference to the drawings wherein like reference numerals designate identical or corresponding elements in each of the several views.

Figure 6:
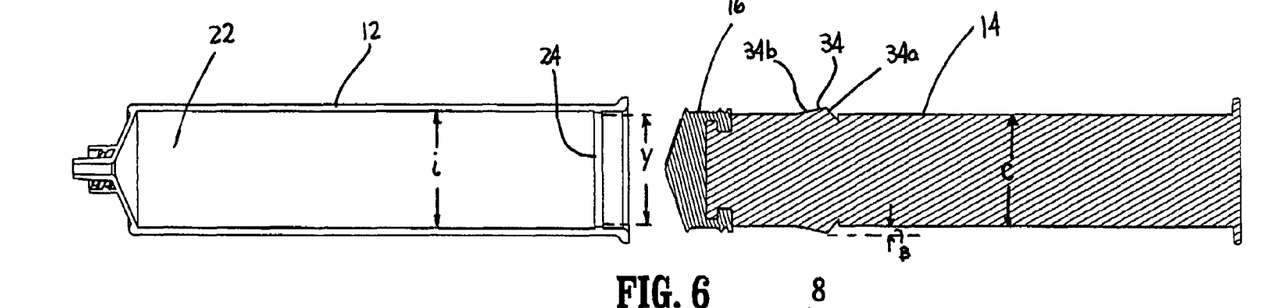
FIG. 6 is a side cross-sectional view of a syringe with the plunger rod shown in FIG. 5 with parts separated.
Figure 7:
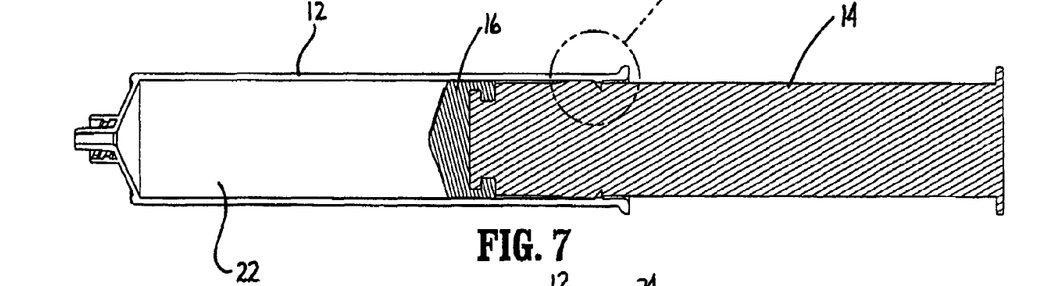
FIG. 7 is a side cross-sectional view of the syringe shown in FIG. 6 with the plunger rod positioned within the syringe barrel.

Referring to FIGS. 1, 2 and 6, syringes 10 includes a syringe barrel 12 defining a reservoir 22 and having an inner diameter "i". A stop 24 or limiting structure is formed on an internal surface of reservoir 22. Stop 24 may include an annular or semi-annular protrusion or one or more spaced protrusions. Stop 24 defines an inner diameter "y" which is less than "i". A plunger rod 14 having a plunger tip 16 supported on the distal end of the plunger rod 14 is slidably positioned within reservoir 22.

Figure 3:
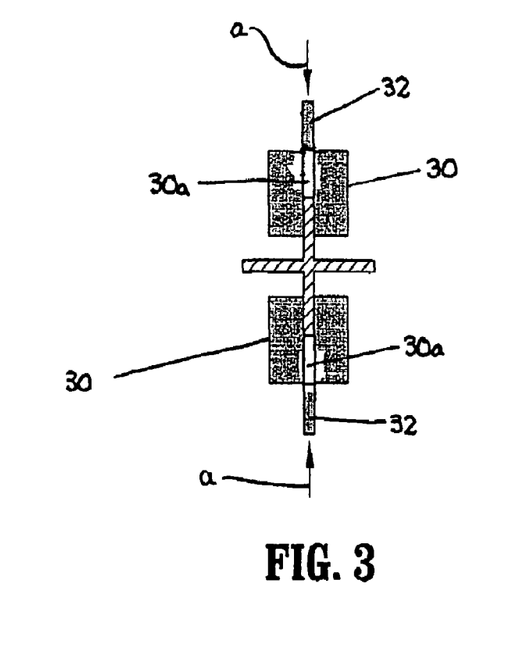
FIG. 3 is a front cross-sectional view of a distorting tool in the process of deforming portions of the plunger rod of the syringe shown in FIG. 2 during one embodiment of the presently disclosed process for creating a stop on a syringe plunger rod.
Figure 4:
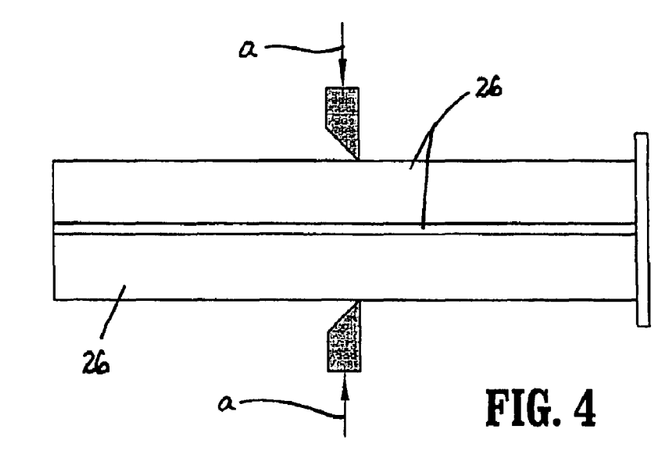
FIG. 4 is a side view of the distorting tool and plunger rod shown in FIG. 3.
Figure 5:
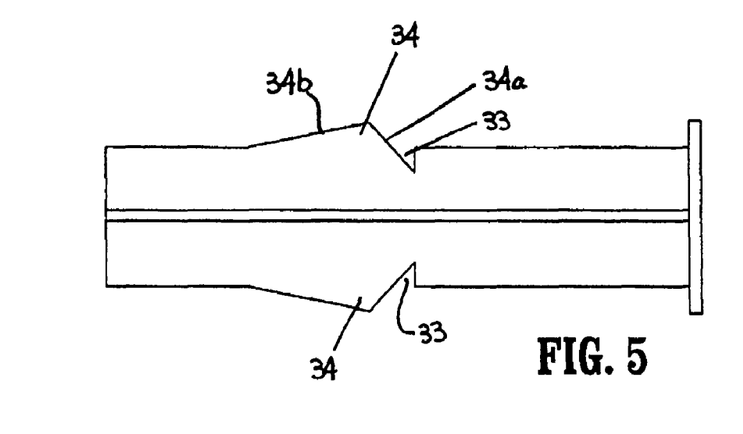
FIG. 5 is a side view of the plunger rod having stops created using the presently disclosed process.
Figure 8:
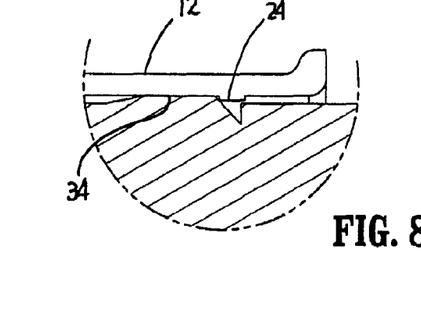
FIG. 8 is an enlarged view of the indicated area of detail shown in FIG. 7.

As illustrated, in one embodiment, plunger rod 14 includes a body having a plurality of orthogonal ribs 26 which define a "+"-shaped cross-section. During one embodiment of the presently disclosed in-line process shown in FIGS. 3-5, one or more of the ribs 26 can be positioned within a slot 30a in a fixture 30. Preferably, slot 30a confines ribs 26. Next, a distorting or swedging tool 32 is pressed in the direction of arrow "a" into the slot or slots 30a to engage and deform a side edge 26a of one or more of ribs 26 of plunger rod 14 to form an indentation 33 and a radial deformation 34 on rib 26. Distorting tool 32 can be in the form of a heated member or having an angled face 32a which creates a radial deformation that has a steeper slope on a proximal side 34a of deformation 34 than on its distal side 34b. Alternately, blade or member 32 can be energized with RF or ultrasonic energy or strictly a mechanical operator. The configuration of radial deformation 34 facilitates easy insertion of plunger rod 14 into reservoir 22 past stop 24 of barrel 12 (FIG. 6), while providing a secure stop to preclude withdrawal of plunger rod 14 beyond stop 24 (See FIG. 8).

The width C of plunger rod 14 added to the outward radial deformation β of radial deformation 34 should be less than the internal diameter i of barrel 12, i.e., i>C+β. This prevents interference between radial deformation 34 and the internal surface of plunger rod 14 during normal operation of syringe 10.

Figure 9:
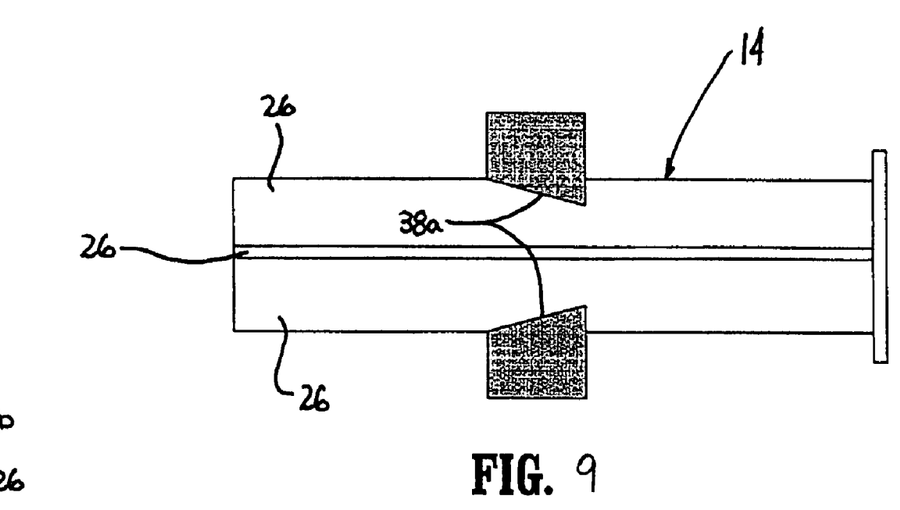
FIG. 9 is a side cross-sectional view of a distorting tool in the process of deforming portions of the plunger rod of the syringe shown in FIG. 2 during another embodiment of the presently disclosed process for creating a stop on a syringe plunger rod.
Figure 10:
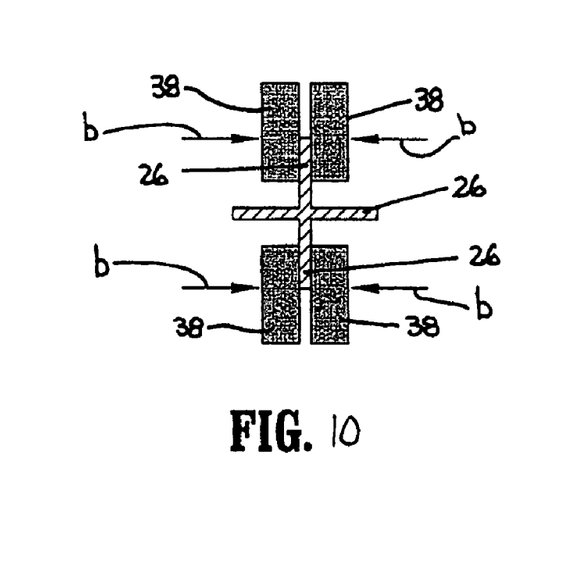
FIG. 10 is a front cross-sectional view of the distorting tool and plunger rod shown in FIG. 9.
Figure 11:
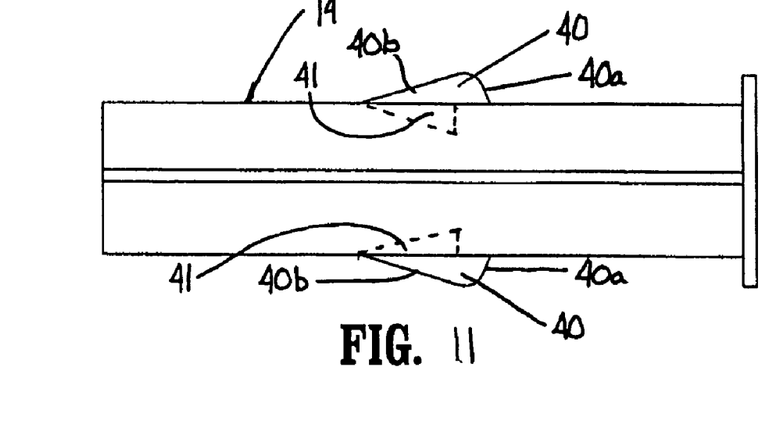
FIG. 11 is a side view of the plunger rod having stops created using the presently disclosed process.

FIGS. 9-11 illustrate an alternate embodiment of the presently disclosed inline process for creating a stop on a plunger rod of a syringe. As illustrated in FIG. 9, plunger rod 14 is identical to the above-described plunger rod. In this process, a pair of dies 38 are moved inwardly in the direction indicated by arrows "b", FIG. 10, on opposite sides of one or more of ribs 26 to deform one or more of ribs 26 to create a radial deformation 40 and resulting indentation 41 shown in phantom. Dies 38 can include angled distal surfaces 38a which are configured to create a radial deformation 40 which has a steeper proximal slope 40a and a less steep distal slope 40b. The less steep distal slope 40b facilitates easy plunger rod insertion into reservoir 22 of barrel 12 while the steeper proximal slope 40a provides a secure stop to prevent plunger withdrawal beyond the predefined stop surface of barrel 12.

Figure 12:
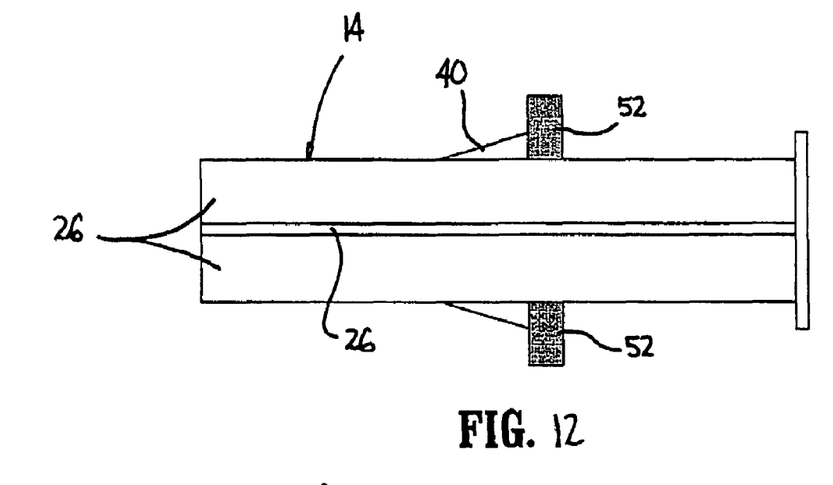
FIG. 12 is a side view of the plunger rod shown in FIG. 11 and a shaping tool during an additional stop of the presently disclosed process.
Figure 13:
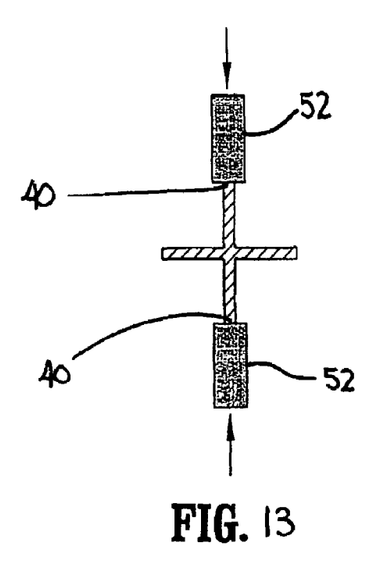
FIG. 13 is a front cross-sectional view of the plunger rod and shaping tool shown in FIG. 12.
Figure 14:
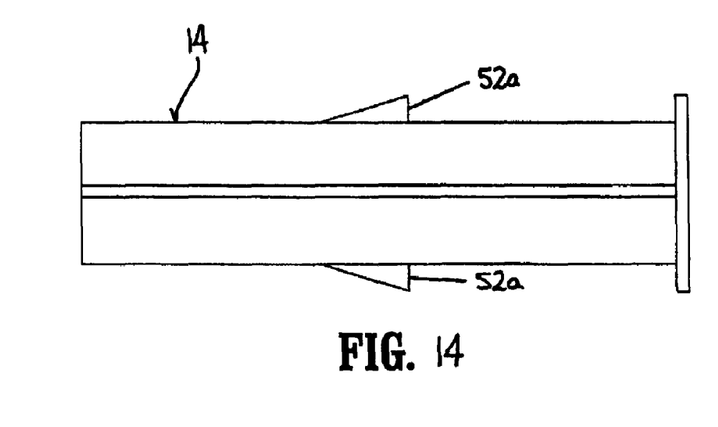
FIG. 14 is a side view of the plunger rod created using the presently disclosed process.

Referring to FIGS. 12-14, additional machining steps can be performed to provide a more effective stop surface. For example, the proximal side of radial deformation 40 (or radial deformation 34) can be machined further to provide a steeper proximal edge, e.g., ninety degree. This can be accomplished using any known machining process including grinding, cutting, melting, etc. In one embodiment, a shaping tool, e.g., heated blocks or cutters 52, can be used to provide a steeper, e.g., 90 degrees, proximal edge 52a of radial deformation 40 (or radial deformation 34). Alternately, proximal edge 52a can be selectively sloped to provide an effective stop surface, preferably, 60-90 degrees.

Limiting structure or stop surfaces on the barrel and the plunger rod may be provided to achieve a number of objectives. Such objectives include simply to prevent disengagement of the barrel and plunger rod or to limit the amount of fluid the syringe can withdraw or expel. Another objective which will be discussed in detail below is to prevent a sterilized region of the syringe barrel to become exposed to an unsterilized region of the syringe.

Figure 15:
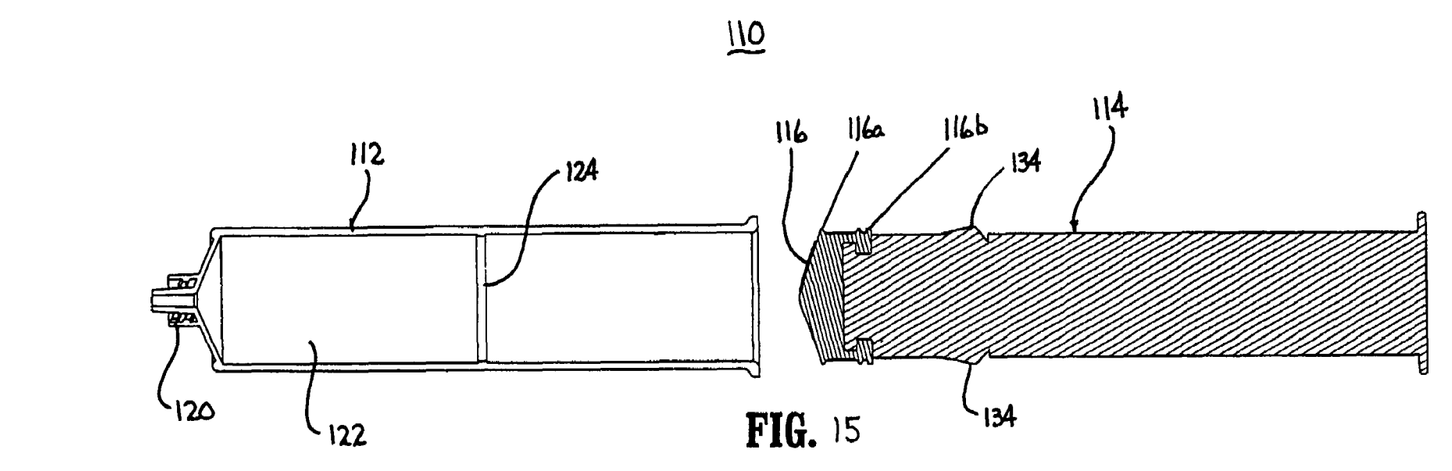
FIG. 15 is a side cross-sectional view of a syringe having a plunger rod having stops created using one of the presently disclosed processes with parts separated.
Figure 16:
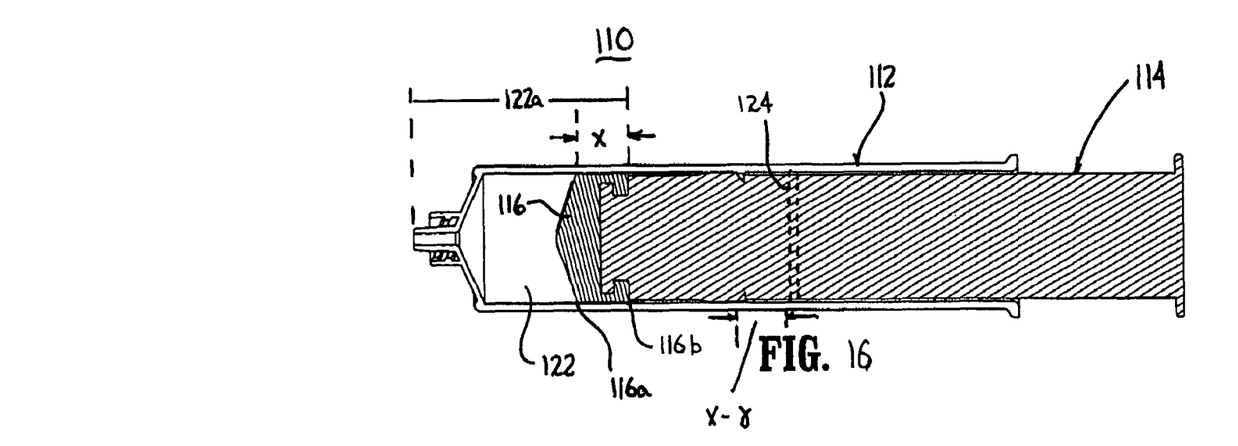
FIG. 16 is a side cross-sectional view of the syringe shown in FIG. 15 with the plunger rod positioned within the syringe barrel.

When a syringe 110 (See FIGS. 15 and 16) is packaged, plunger rod 114 is positioned within reservoir 22 of barrel 112 (FIG. 16). Although not shown, a cap is provided on connector 120. Plunger tip 116 includes a distal sealing surface 116a and a proximal sealing surface 116b. A distance "x" is defined between distal sealing surface 116a and proximal sealing surface 116b. Although syringe 110 is sterilized prior to packaging, typically, the packaging does not maintain sterility. Thus, only the sterile region 122a of reservoir 122 between proximal sealing surface 116b and the cap (not shown) remains sterile.

Because the proximal portion of reservoir 122 is not sterile, for obvious reasons, it is not desirable to expose sterile portion 122a of reservoir 122 to the unsterilized portion of reservoir 122 positioned proximally of sterile portion 122a. To prevent this from occurring, a stop surface 134 is formed on plunger rod 114. Stop surface 134 is positioned on plunger rod 114 to engage stop surface 124 on the inner surface of barrel 112 to prevent distal sealing surface 116a from being retracted within reservoir 122 proximally beyond the original location of proximal sealing surface 116b (which defines the proximal end of sterile region 122a of reservoir 122). More specifically, stop surface 134 and stop surface 124 are positioned apart a distance of x– wherein is a small incremental distance. By limiting retraction of plunger rod 114 to a distance of x–, movement of distal sealing surface 116a beyond the original location of proximal sealing surface 116b is prevented.

When syringe 110 is operated by medical personnel, plunger rod 114 is initially advanced slightly to remove air bubbles that may be present within reservoir 122 of barrel 112. When this step is performed, syringe 110 should be positioned with the distal end of barrel 112 at a higher elevation than the proximal end of barrel 112. Next, plunger rod 114 is retracted to draw blood into the medical device, e.g., needle or catheter (not shown), to which the syringe is attached. By drawing blood into the medical device, medical personnel can confirm that an open flow path exists between the patient's vasculature and syringe barrel. During this step, stop surface or surfaces 134 engage stop surface or surfaces 124 to prevent over retraction of plunger rod 114 which would result in contamination of sterile portion 122a of syringe 110. Thereafter, plunger rod 114 is advanced distally within barrel 112 to dispense fluid from within sterile portion 122a of reservoir 122 into the patient.

It will be understood that various modifications may be made to the embodiments disclosed herein. For example, the shape of the stop surface created and the instruments used to create the stop surface can be selectively chosen and need not be as disclosed herein. Further, it is envisioned that the above disclosed processes can be used to create one or more stop surfaces, e.g., one to four, on the plunger rod. Therefore, the above description should not be construed as limiting, but merely as exemplifications of preferred embodiments. Those skilled in the art will envision other modifications within the scope and spirit of the claims appended hereto.

What is claimed is:

1. A process for creating a stop surface on a syringe plunger rod, the process comprising the following steps:
   a) molding a plunger rod having a distal end adapted to support a plunger tip which is dimensioned to be slidably positioned within a reservoir of a syringe barrel, and
   b) forming a radially-extending deformation on the molded plunger rod by creating an indentation in the plunger rod and displacing material forming the plunger rod to define the radially-extending deformation;
   wherein the forming step includes providing a swedging tool configured such that the radial deformation formed as sloped proximal and distal surfaces, wherein the proximal surface defines a steeper slope than the distal surface.

2. A process according to claim 1, wherein the step of forming includes the step of pressing a swedging tool into a sidewall of the molded plunger rod to form the radial deformation and the indentation in the plunger rod.

3. A process according to claim 2, wherein the molded plunger rod includes a +-shaped body defining a plurality of orthogonal ribs and the step of pressing includes the step of pressing the swedging tool into a side edge of one or more of the orthogonal ribs.

4. A process according to claim 3, wherein the step of pressing includes the step of pressing the swedging tool into the side edge of two or more of the orthogonal ribs.

5. A process according to claim 1, wherein the swedging tool is heated.

6. A process according to claim 1, further including the step of shaping the radial deformation to provide a steeper proximal edge.

7. A process according to claim 6, wherein the shaping step includes shaping the radial deformation to define a proximal edge having a slope of between about sixty degrees and about ninety degrees.

8. A process for creating a stop surface on a syringe plunger rod, the process comprising the following steps:
   a) molding a plunger rod having a distal end adapted to support a plunger tip which is dimensioned to be slidably positioned within a reservoir of a syringe barrel; and
   b) forming a radially-extending deformation on the molded plunger rod, the radially-extending deformation having sloped proximal and distal surfaces, wherein the proximal surface defines a steeper slope than the distal surface.

9. A process according to claim 8, wherein the step of forming includes the step of creating an indentation in the plunger rod and displacing material forming the plunger rod to define the radially-extending deformation.

* * * * *